United States Patent [19]

Mori et al.

[11] Patent Number: 4,605,742

[45] Date of Patent: Aug. 12, 1986

[54] PROCESS FOR THE PRODUCTION OF PIPERIDINE

[75] Inventors: Shoichiro Mori; Tadamichi Aoki; Ryozo Hamana; Yutaka Nomura, all of Ibaraki, Japan

[73] Assignee: Mitsubishi Petrochemical Co., Ltd., Tokyo, Japan

[21] Appl. No.: 699,125

[22] Filed: Feb. 7, 1985

[30] Foreign Application Priority Data

Feb. 13, 1984 [JP] Japan .................................. 59-22901

[51] Int. Cl.$^4$ .......................................... C07D 295/02
[52] U.S. Cl. ..................................................... 546/184
[58] Field of Search ........................................ 546/184

[56] References Cited

U.S. PATENT DOCUMENTS 2,265,201 12/1941 Schmidt et al. ...................... 546/184
4,544,749 10/1985 Ayusawa et al. .................... 546/184

OTHER PUBLICATIONS

Chemical Abstracts, 40:3757$^9$ (1946) [Paul et al., Compt. Rend. 221, 560-2 (1945)].
Kline, C., et al., J. Am. Chem. Soc., 66, 1710 (1944).
Wilson, C., J. Am. Chem. Soc., 67, 693 (1945).

Primary Examiner—Richard A. Schwartz
Attorney, Agent, or Firm—Oblon, Fisher, Spivak, McClelland & Maier

[57] ABSTRACT

A process for the production of piperidine by catalytic hydrogenation of furfurylamine and/or tetrahydrofurfurylamine in the presence of a hydrogenation catalyst by flowing hydrogen gas into a reaction zone, wherein the starting material is introduced into a liquid phase in the reaction zone, the liquid phase being maintained at a constant temperature, and the reaction product is withdrawn from the reaction zone in a gaseous form together with excess hydrogen gas.

16 Claims, 1 Drawing Figure

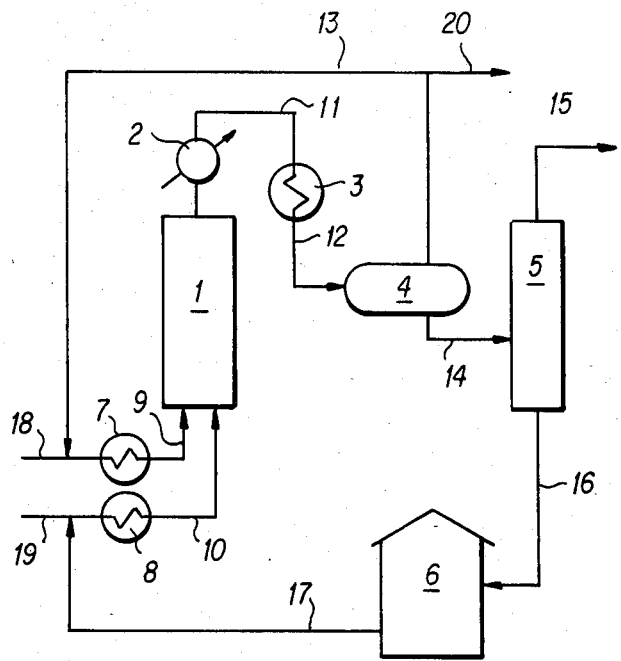

PROCESS FOR THE PRODUCTION OF PIPERIDINE

FIELD OF THE INVENTION

The present invention relates to a process for the production of piperidine. More particularly, it is concerned with a process for the production of piperidine by catalytic hydrogenation of furfurylamine (hereinafter sometimes abbreviated to "FAM") and/or tetrahydrofurfurylamine (hereinafter sometimes abbreviated to "4HFAM").

BACKGROUND OF THE INVENTION

Piperidine is a 6-membered alicyclic amine and is a useful organic compound as an intermediate for use in preparation of various organic compounds such as medicines, agricultural chemicals, and rubber chemicals. From a viewpoint of extending the uses of these organic compounds, a technique permitting industrial production of piperidine at low costs is very valuable. Thus it has been desired to develop such a process for the production of piperidine.

It is well known that piperidine is produced by hydrogenation of pyridine. Since, however, pyridine is relatively expensive, many methods have been proposed to produce piperidine from starting materials other than pyridine: a method in which 1,5 pentanediamine is used as the starting material and is subjected to a cyclization reaction to produce piperidine, a method in which piperidine is produced by the ammonolysis reaction of tetrahydropyran, 1,5-pentanediol, or tetrahydrofurfuryl alcohol, for example, and a method in which piperidine is produced by the hydrogenation reaction of FAM or 4HFAM. These methods, however, have disadvantages in that the starting materials are not readily available, the reactions must be carried out at high temperatures, the yield is low, and the processes are complicated and not economical. Thus these method have not yet been put into a practical process.

Of the starting materials used in the above-described methods, FAM and 4HFAM are readily available and are not expensive, because FAM can be produced in good yields by reductive ammonolysis of furfural which is obtained in large amounts from agricultural products, and 4HFAM can also be produced in good yields by hydrogenation of FAM. Thus, the method of producing piperidine by hydrogenation of FAM or 4HFAM is believed to become an industrially useful method so long as piperidine can be produced in good yields.

U.S. Pat. No. 2,265,201 describes that piperidine can be produced in "good yields" (numerical values are not disclosed) if liquid ammonia is added to FAM and a batchwise hydrogenation reaction of FAM is carried out in the presence of a cobalt catalyst, the amount of the cobalt catalyst being one-tenth (by weight) of the starting material, at a temperature of 250° C. under a pressure of 200 atms for 10 minutes. Also, in the case of 4HFAM, it is described that piperidine can be produced in "good yields" as in FAM. In addition, it is described that even when copper chromite and nickel catalysts are used, piperidine can be produced in "good yields" in a reaction system with ammonia added thereto under high temperature/high pressure conditions. Moreover, it is described that a platinum catalyst can be used (although any examples showing the use thereof are not disclosed), and that in the case of a liquid phase reaction, the use of inert solvents such as methanol and cyclohexane are advantageous (although any examples supporting this fact are not disclosed).

Thereafter, it was reported that piperidine was produced in a yield of 9% by hydrogenating FAM in a reaction system not containing ammonia under a pressure of at least 100 atmospheric pressure in the presence of Raney nickel (J. Am. Chem. Soc., Vol. 67, page 693 (1945)), and in a yield of 11% by the use of a copper chromite catalyst (Acta, Chem. Scand., Vol. 20, page 591 (1966)).

In order to quantitatively examine the contents disclosed in U.S. Pat. No. 2,265,201, the procedure of Example 2 was repeated wherein a Raney cobalt catalyst was used and the reaction pressure was changed to 135 atmospheric pressure. It was found that the conversion of FAM was 99.9% but the yield of piperidine was only 22%; the major portion of the FAM was converted into high boiling point products. In addition, in view of the disclosure that methanol is useful as a solvent, the same procedure as above was repeated with the addition of methanol. In this case, however, it was found that the yield of piperidine was lower.

As described above, a severe reaction condition, i.e., a reaction pressure as high as 100 atmospheric pressure is needed in hydrogenation of FAM and/or 4HFAM, and the desired product, piperidine, can be produced only in extremely low yields. Thus, the catalytic hydrogenation of FAM and/or 4HFAM has not yet been developed to such an extent that such is industrially usable.

SUMMARY OF THE INVENTION

As a result of extensive investigations on analysis of the reaction behaviours of FAM and 4HFAM, various reaction products, etc., the inventors have established a process for efficiently producing piperidine by catalytic hydrogenation of FAM and/or 4HFAM under very mild conditions as compared with those in the conventional methods.

Accordingly, an object of the present invention is to provide a process for producing piperidine which comprises catalytically hydrogenating furfurylamine and/or tetrahydrofurfurylamine, wherein the starting material, furfurylamine and/or tetrahydrofurfurylamine, is introduced into a liquid in a reaction zone, said liquid being maintained at a constant temperature, and the reaction product is withdrawn from the reaction zone in a gaseous form along with excess hydrogen gas.

BRIEF DESCRIPTION OF THE DRAWING

The FIGURE is a flow chart showing one embodiment of the process of the present invention.

1 . . . Reactor, 4 . . . Separator, 5 . . . Separator, 6 . . . Tank.

DETAILED DESCRIPTION OF THE INVENTION

When FAM is placed under conditions for hydrogenation of 4HFAM, the furan ring of FAM is usually hydrogenated relatively promptly and FAM is converted into 4HFAM. In the hydrogenation reaction of 4HFAM, the oxygen-carbon bond of the furan ring is first cleaved, resulting in opening of the furan ring and, thereafter, intramolecular dehydration occurs to form a nitrogen-containing 6-membered compound, piperidine. If, however, the bond between the carbon in the 5-position of the furan ring and the oxygen is cleaved, undesirable by-products such as n-amylamine are formed. 5-Aminopentanol which is an intermediate in the formation of piperidine is formed depending on reaction conditions. In general, the starting material and reaction products, FAM, 4HFAM, 5-aminopentanol, and piperidine, are very reactive under hydrogenation conditions, and these amines react with each other to form various polycondensates.

In particular, the desired product, piperidine, is very reactive and in the batchwise reaction, piperidine once formed undergoes a polycondensation reaction at a later stage of the reaction where the conversion of 4HFAM is high, resulting in a considerable reduction in the selectivity of piperidine. As a result of analysis of the polycondensates, N-tetrahydrofurfurylpiperidine, N-n-pentylpiperidine, 1,5-dipiperidinylpentane, N-furfurylpiperidine, etc. are formed.

As a result of extensive investigations based on the understanding that the reduction of selectivity in the above described reaction is ascribable mainly to the successive reaction of piperidine, it has been found that if the desired product, piperidine, is withdrawn quickly from the reaction mixture together with excess hydrogen gas, the successive reaction of piperidine can be efficiently prevented.

The present invention will hereinafter be explained in detail by reference to the accompanying drawing.

The FIGURE shows a flow chart of one embodiment of the process of the present invention. The starting material, FAM and/or 4HFAM, is introduced through a pipe 19 and combined with FAM and 4HFAM recycled through a pipe 17, and the resulting mixture is then preheated in a preheater 8 and introduced through a pipe 10 into a reactor 1 which contains as a reaction zone a liquid with a catalyst suspended therein. Hydrogen gas is preheated in a preheater 7 and then introduced through a pipe 9 into the reactor 1. The reactor is equipped with a suitable stirrer. The vapor effluent from the reactor 1 is introduced through a pipe 11 into a condenser 3 where an oily component is condensed and, thereafter, sent through pipe 12 to gas-liquid separator 4 where the effluent is separated into a gaseous phase and a condensed phase. A reflux condenser 2 is provided so that the unreacted starting material can be returned to the reactor 1 by controlling the ratio of the amount of light reaction products such as piperidine to the amount of the starting material, which are contained in the vapor effluent from the reactor 1.

The gas phase from the gas-liquid separator is composed mainly of hydrogen, and part of the gas phase is discharged through a pipe 20 and the remainder is recycled through a pipe 13 to the reactor 1. The liquid phase is sent to a separator 5 where it is separated into the starting material and the reaction products including piperidine. The reaction products are sent through a pipe 15 to a purification unit (not shown). The above-separated fraction composed mainly of the starting material is sent through a pipe 16 to a tank 6. This unreacted starting material can be again introduced into the reactor 1.

Various modifications can be made to the apparatus shown in the FIGURE. For example, the reflux condenser 2 is removed, and all the unreacted starting material contained in the vapor effluent can be separated in the separator 5 and recycled. That is, the present invention is not limited to the embodiment shown in the FIGURE, and various changes and modifications can be made without departing from the spirit and scope of the present invention.

In accordance with the process of the present invention, side reactions such as polycondensation of the desired product, piperidine, or the starting material, for example, can be prevented efficiently and piperidine can be produced in good yields. Another advantage of the present invention is that the control of heat of reaction can be facilitated. Still another advantage is that the concentrations of by-produced water, ammonia, and piperidine, for example, in the catalyst suspension decrease so that the rate of the desired reaction can be increased.

The conventionally used hydrogenation catalysts can be employed in the present invention. Examples thereof include cobalt-based, nickel-based, ruthenium-based, rhodium-based, palladium-based, platinum-based, iridium-based, and copper chromite-based catalysts. These catalysts may or may not be deposited on a carrier. A preferred example of such hydrogenation catalysts is a cobalt-based catalyst. Specific example of the cobalt-based catalyst is Raney cobalt.

The Raney cobalt is developed with an alkali in its aqueous solution by the usual procedure. After the development, the Raney cobalt is washed until no alkali ions are detected. After replacement of the water in the Raney cobalt with a solvent which is used in the hydrogenation reaction, the Raney cobalt is used. If the solvent used in the hydrogenation reaction is not compatible with water, the water is once replaced with water-soluble and lipophilic solvent and is then replaced with the desired solvent. The Raney cobalt may contain co-catalyst metals such as manganese, iron, nickel, copper, molybdenum, tungsten, rhenium, and chromium. The preferred amount of the co-catalyst metal added is that the atomic ratio of each co-catalyst metal to cobalt be from about 0.01:1 to about 0.3:1.

Another preferred example of the cobalt-based catalyst is a reduced cobalt. This reduced cobalt is usually prepared by heating cobalt oxide in a stream of reducing gas such as hydrogen. The cobalt oxide is obtained by decomposition of cobalt salts such as cobalt carbonate, cobalt hydroxide, and cobalt nitrate, from which coexisting functional groups are removed upon decomposition thereof. The reduced cobalt can be obtained in the form that such is deposited on a carrier. The reduced cobalt deposited on a carrier can be prepared by adding the carrier in preparation of the cobalt salt, or by mixing the carrier with the cobalt salt or cobalt oxide and then subjecting the resulting mixture to a reduction treatment. Preferred examples of carriers which can be used include diatomaceous earth, silica, alumina, zirconia, and magnesia. If desired and necessary, the reduced cobalt deposited on the carrier may be molded. The reduced cobalt may contain co-catalysts.

In the preparation of the above catalyst, the reduction process is usually carried out in a stream of hydrogen at a temperature of from 150° to 500° C., preferably from 200° to 300° C. After the reduction, the catalyst is used under the condition which is shielded from the air. A method of shielding the catalyst by impregnating it with the reaction solvent is simple and convenient. If desired and necessary, the catalyst may be made such that the catalyst can be handled in the air without spontaneous ignition, by subjecting it to a so-called stabilization treatment, i.e., by gradually contacting the reduced product with air or carbon dioxide gas, for example, in an inert gas.

The hydrogenation catalyst is suspended in a solvent which is liquid under the reaction conditions. The concentration of the hydrogenation catalyst in the suspension is from 0.001 to 30% by weight and preferably from 0.01 to 20% by weight based on the weight of the suspension In general, the catalyst has higher activity at an earlier stage of the reaction. Therefore, a procedure is employed, in which the reaction is carried out in a low concentration at an earlier stage thereof, and when the catalytic activity drops to a certain level, the catalyst is supplemented and the reaction is continued at a higher concentration.

As the solvent which can be used in the present invention, any commonly used solvents can be employed so long as they are liquid under the reaction conditions and, furthermore, unless their boiling points are extremely near the boiling point of the reaction product (i.e., piperidine), they are hydrocracked under the reaction conditions, they seriously deterioate the performance of the catalyst, or they are very reactive with the starting material and the reaction product, thereby accelerating the side reactions. In general, solvents having a boiling point higher than that of piperidine are used from a standpoint of process.

Solvents which can be used include hydrocarbon compounds, oxygen-containing compounds, and nitrogen-containing compounds.

Representative examples of the hydrocarbon compounds are saturated aliphatic hydrocarbons such as n-octane, n-nonane, n-decane, n-dodecane, 2,7-dimethyloctane, and fluid paraffin: saturated alicyclic hydrocarbons such as 1,3-dimethylcyclohexane, and 1,4-diisopropylcyclohexane; and aromatic hydrocarbons such as tetralin, indane, and octahydroanthracene.

Representative examples of the oxygen-containing compounds are alcohols such as 1-pentanol, 2-ethylhexanol, 1-dodecanol, cyclohexanol, 2-methyl-2-butanol, and 2-methyl-2-hexanol; and ethers such as dibutyl ether, diamyl ether, diisoamyl ether, dicyclohexyl ether, methyl cellosolve, ethyl cellosolve, butyl cellosolve, and 1,4-butanediol monomethyl ether. These ethers encompass glycol dialkyl ethers. In the case of monoglycol dialkyl, it is preferred that the glycol portion contain from 2 to 4 carbon atoms, and the number of carbon atoms in the alkyl moiety be from 1 to 5 (alkyl groups having 3 or more carbon atoms may be branched). In polyethylene glycol dialkyl ethers as one group of the ethers, the alkyl group is the same as described above, and the number of carbon atoms in the connected ethoxy group is from 2 to 6 and preferably from 2 to 4. The ethers encompass cyclic ethers. Representative examples of such cyclic ethers are dioxane and tetrahydrofuran.

Of the above oxygen-containing compounds, ethers not containing a hydroxyl substituent provides good results as a solvent.

As nitrogen-containing compounds, tert-amines (particularly saturated amines) are preferred. Examples of such tert-amines are tripropylamine and tributylamine. Alkyl groups substituted at the nitrogen atoms may be the same or different. N-alkyl-substituted cyclic imines such as N-pentyl-piperidine are preferably used. An ether bond may be present in the ring. An example of such ether bond-containing compounds is N-alkyl-substituted morpholine. In addition, part or all of the polycondensate by-produced can be used as the solvent.

Hydrogenation conditions can be determined appropriately so that problems do not occur in the practice of the process of the present invention. The reaction temperature is from about 100° to 400° C. and preferably from about 150° to 300° C. The reaction pressure is from atmospheric pressure to 200 atmospheric pressure and preferably from 2 to 100 atmospheric pressure. The flow rate of hydrogen is one sufficient to withdraw the reaction product from the reaction zone. Usually, hydrogen is introduced at such a flow rate that the molar ratio of hydrogen to the starting material is from 1:1 to 10,000:1 and preferably from 2:1 to 5,000:1.

The starting material may be any one of furfurylamine and tetrahydrofurfurylamine, or a mixture thereof. In addition, the starting material may be introduced into the reactor in combination with the unreacted starting material or further with a recycle containing the reaction intermediate and by-products.

The present invention is described in greater detail by reference to the following non-limiting examples.

PREPARATION EXAMPLE 1

Preparation of Catalyst

To an aqueous solution of 150 g of cobalt nitrate ($Co(NO_3)_2 \cdot 6H_2O$) dissolved in 175 ml of distilled water was added dropwise an aqueous solution of 141 g of ammonium hydrocarbonate ($NH_4HCO_3$) dissolved in 650 ml of distilled water over 2 hours while stirring and maintaining at 20° to 22° C. Basic cobalt carbonate precipitated was filtered off and thoroughly washed with distilled water to yield a basic cobalt carbonate salt cake (Co-content: 9.09% by weight). To 165 g of the above-prepared cake (containing 15 g of cobalt) were added 1.96 g of ammonium perrhenium ($NH_4ReO_4$) and 6.7 g of ammonium molybdate ($(NH_4)_6Mo_7O_{24}$) both in the form of an aqueous solution, and the resulting mixture is fully kneaded and then dried while heating at about 80° C. The thus-obtained powder was dried at 100° to 110° C. for 12 hours, further dried at 450° C. for 1 hour in a stream of air, and then reduced at 300° C. for 2 hours in a stream of hydrogen to yield a cobalt/rhenium/molybdenum catalyst (Co:Re:Mo=1:0.03:0.015 (atomic ratio)).

PREPARATION EXAMPLE 2

17 g of Raney cobalt-manganese alloy (Co:Mn:Al=30:3.5:66.5) was gradually added to a 25% aqueous NaOH solution at room temperature while stirring so that a rapid heat generation did not occur. The resulting mixture was heated to 50° C. while stirring and after 1 hour, the mixture was subjected to decantation. The decantation washing was further repeated 10 times with 200 ml of hot water, followed by washing 5 times with 200 ml of dioxane to obtain a Raney cobalt-manganese catalyst.

EXAMPLE 1

In this example, the equipment shown in the FIGURE was used.

Into a reactor 1 (inner volume: 300 ml) was introduced 150 ml of fluid paraffin, and 1.0 g of the cobalt/rhenium/molybdenum catalyst prepared in Preparation Example 1 was dispersed in the fluid paraffin. The reactor 1 was heated while feeding a small amount of hydrogen through a pipe 9 so that the reaction temperature was 190° C. and the temperature in the reflux condenser 2 was 150° C. The reaction pressure was set at 30 kg/cm², and the flow rate of hydrogen in a gas outlet pipe 20 was controlled to 150 Nl/hr (the recycle of the gas through a pipe 13 was not performed in this example). 4HFAM was then introduced into the reactor 1 through a pipe 10 at a flow rate of 102.7 mmol/hr. Liquid products from a pipe 14 were collected and analyzed by a gas chromatography. In several hours from the initiation of the reaction, the reaction started to proceed in a steady state or stabilized manner. After 4 hours from the steady state, the liquid products were analyzed. This analysis showed that the one-path conversion of 4HFAM was 89.0 mol % and the selectivity of piperidine from the converted 4HFAM was 84.3 mol %. The selectivities of products other than piperidine from the converted 4HFAM were as follows: 0.5 mol % for n-amylamine, 1.0 mol % for methyltetrahydrofuran, and 9.1 mol % for polycondensates. At this time, the liquid phase in the reactor contained, as well as a trace of water, 0.4% by weight of 4HFAM, 1.8% by weight of FAM, and 2.98% by weight of polycondensates.

EXAMPLE 2

The procedure of Example 1 was repeated except that 4HFAM was replaced by FAM. The results obtained were as follows.
One-path conversion of FAM: 88.5 mol %
Selectivity of piperidine: 77.8 mol %
Selectivity of n-amylamine: 6.7 mol %
Selectivity of 2-methyltetrahydrofuran: 3.6 mol %
Selectivity of polycondensates: 8.3 mol %
(all the selectivities are based on the converted FAM).

EXAMPLE 3

The procedure of Example 1 was repeated except that the reaction temperature was changed to 210° C. The results obtained were as follows.
One-path conversion of 4HFAM: 98.4 mol %
Selectivity of piperidine: 78.4 mol %
Selectivity of n-amylamine: 1.8 mol %
Selectivity of 2-methyltetrahydrofuran: 3.6 mol %
Selectivity of polycondensates: 10.1 mol %
(all the selectivities are based on the converted 4HFAM).

EXAMPLE 4

The procedure of Example 1 was repeated except that the fluid paraffin was replaced by 150 ml of tetragrime (tetraethylene glycol dimethyl ether). The results obtained were as follows.
One-path conversion of 4HFAM: 76.6 mol %
Selectivity of piperidine: 91.6 mol %
Selectivity of n-amylamine: 0.5 mol %
Selectivity of 2-methyltetrahydrofuran: 1.0 mol %
Selectivity of polycondensates: 4.8 mol %
(all the selectivities are based on the converted 4HFAM).

EXAMPLE 5

The procedure of Example 1 was repeated except that the fluid paraffin as a solvent was replaced by 150 ml of tetragrime, and 4HFAM as a starting material was replaced by FAM. The results obtained were as follows.
One-path conversion of FAM: 86.4 mol %
Selectivity of piperidine: 79.3 mol %
Selectivity of n-amylamine: 6.8 mol %
Selectivity of 2-methyltetrahydrofuran: 3.6 mol %
Selectivity of polycondensates: 8.0 mol %
(all the selectivities are based on the converted FAM).

EXAMPLE 6

The procedure of Example 1 was repeated except that 2.0 g of the Raney-cobalt-manganese catalyst prepared in Preparation Example 2 was used in place of 1.0 g of the cobalt/rhenium/molybdenum catalyst. The results obtained were as follows.
One-path conversion of 4HFAM: 93.3 mol %
Selectivity of piperidine: 91.1 mol %
Selectivity of n-amylamine: 0.5 mol %
Selectivity of 2-methyltetrahydrofuran: 2.1 mol %
Selectivity of polycondensates: 6.2 mol %
(all selectivities are based on the converted 4HFAM).

COMPARATIVE EXAMPLE 1

In this example, a batch-wise autoclave was used.
The autoclave (inner volume: 50 ml) was charged with 10 g of 4HFAM and 1 g of the same catalyst as in Example 1. After the atmosphere in the autoclave was replaced with hydrogen gas, the reaction temperature was set at 210° C. and the temperature was raised. When the reaction temperature reached 210° C., the hydrogen pressure was set at 60 kg/cm$^2$G and the reaction was conducted for 1 hour. After the autoclave was cooled, the reaction mixture was analyzed by a gas chromatography. The results obtained were as follows.
One-path conversion of 4HFAM: 92.6 mol %
Selectivity of piperidine: 45.9 mol %
Selectivity of n-amylamine: 0.3 mol %
Selectivity of polycondensates: 53.8 mol %
(all the selectivities are based on the converted 4HFAM).

While the invention has been described in detail and with reference to specific embodiments thereof, it will be apparent to one skilled in the art that various changes and modifications can be made therein without departing from the spirit and scope thereof.

What is claimed is:

1. A process for the production of piperidine, comprising:
    continuously introducing hydrogen and liquid furfurylamine, tetrahydrofurfurylamine or a mixture thereof into a reaction zone;
    hydrogenating said furfurylamine, tetrahydrofurfurylamine or mixture thereof reactant while maintaining liquid phase conditions within the reaction zone in the presence of a hydrogenation catalyst at a constant temperature; and
    continuously withdrawing product piperidine from the reaction zone as a gas with excess hydrogen gas.

2. The process of claim 1, wherein the hydrogenation catalyst is selected from the group consisting of a cobalt-based catalyst, a nickel-based catalyst, a ruthenium-based catalyst, a rhodium-based catalyst, a palladium-based catalyst, a platinum-based catalyst, an iridium-based catalyst and a copper chromite-based catalyst.

3. The process of claim 2, wherein the hydrogenation catalyst is a cobalt-based catalyst.

4. The process of claim 3, wherein the cobalt-based catalyst is selected from the group consisting of a Raney cobalt and a reduced cobalt.

5. The process of claim 1, wherein the hydrogenation catalyst is suspended in a solvent which is liquid at the hydrogenation reaction conditions.

6. The process of claim 5, the concentration of the catalyst in the suspension is 0.001 to 30% by weight based on the weight of the suspension.

7. The process of claim 5, wherein the solvent is a liquid under the reaction conditions.

8. The process of claim 7, wherein the solvent has a boiling point higher than that of piperidine.

9. The process of claim 5, wherein the solvent is selected from the group consisting of a hydrocarbon compound, a oxygen-containing compound and a nitrogen-containing compound.

10. The process of claim 9, wherein the hydrocarbon compound is selected from the group consisting of n-octane, n-nonane, n-decane, n-dodecane, 2,7-dimethyloctane, fluid paraffin, 1,3-dimethylcyclohexane, 1,4-diisopropylcyclohexane, tetralin, indane and actahydroanthrathene.

11. The process of claim 9, wherein the oxygen-containing compound is selected from the group consisting of 1-pentanol, 2-ethylhexanol, 1-dodecanol, cyclohexanol, 2-methyl-2-hexanol, dibytyl ether, diamyl ether, diisoamyl ether, dicyclohexyl ether, methyl cellosolve, ethyl cellosolve, butyl cellosolve and 1,4-butanediol monoethyl ethyl ether.

12. The process of claim 9, wherein the nitrogen-containing compound is a tertiary amine.

13. The process of claim 1, wherein the hydrogenation is conducted at a temperature of 100° to 400° C.

14. The process of claim 1, wherein the hydrogenation is conducted under a pressure of atmospheric pressure to 200 atmospheric pressure.

15. The process of claim 1, wherein the flow rate of the hydrogen gas is one sufficient to withdraw the reaction preduct from the reaction zone.

16. The process of claim 1, wherein the flow rate of the hydrogen gas is such that the molar ratio of hydrogen to the starting material is from 1:1 to 10,000:1.

* * * * *